United States Patent
Buechi et al.

(10) Patent No.: US 9,937,316 B2
(45) Date of Patent: *Apr. 10, 2018

(54) CONNECTING-SYSTEM KIT FOR A RESPIRATORY HUMIDIFIER

(71) Applicant: Hamilton Bonaduz AG, Bonaduz (CH)

(72) Inventors: Rudolf Buechi, Chur (CH); Reto Frei, Bonaduz (CH); Marc Maeder, Malans (CH); Thomas Granzotto, Igis (CH); Axel Zolkos, Felsberg (CH)

(73) Assignee: Hamilton Medical AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/392,109

(22) Filed: Dec. 28, 2016

(65) Prior Publication Data

US 2017/0106162 A1 Apr. 20, 2017

Related U.S. Application Data

(63) Continuation of application No. 14/348,969, filed as application No. PCT/EP2012/069125 on Sep. 27, 2012.

(30) Foreign Application Priority Data

Oct. 1, 2011 (DE) .................. 10 2011 054 134

(51) Int. Cl.
*A61M 16/08* (2006.01)
*A61M 16/16* (2006.01)
(Continued)

(52) U.S. Cl.
CPC .... *A61M 16/0833* (2014.02); *A61M 16/0003* (2014.02); *A61M 16/0057* (2013.01);
(Continued)

(58) Field of Classification Search
CPC .............. A61M 16/0816; A61M 16/16; A61M 16/0051; A61M 16/0875; A61M 16/1075;
(Continued)

(56) References Cited

U.S. PATENT DOCUMENTS

2006/0113690 A1  6/2006 Huddart et al.
2008/0105257 A1  5/2008 Klasek et al.
(Continued)

FOREIGN PATENT DOCUMENTS

EP      2229973 A2 *  9/2010  ........ A61M 16/1045
WO  WO 2009022004 A2 *  2/2009  ............ A61M 16/06

*Primary Examiner* — Todd J Scherbel
*Assistant Examiner* — Elliot S Ruddie
(74) *Attorney, Agent, or Firm* — Jansson Munger McKinley & Kirby Ltd.

(57) ABSTRACT

A liquid-container/ventilation-tube kit for a ventilation system that includes (a) a ventilator, (b) a respiratory humidifier having a housing and a liquid container, the housing having a pair of first electrical contact elements, (c) a first inhalation tube extending from the respiratory humidifier to a Y-piece, (d) a second inhalation tube extending from the ventilator to the respiratory humidifier, and (e) an exhalation tube extending from the Y-piece to the ventilator, the kit including the liquid container having a pair of first connection elements for removable connection of the first and second inhalation tubes thereto, and a pair of second connection elements each attached to a respective one of the first and second inhalation tubes and by which each of the inhalation tubes is pneumatically connected to a respective one of the first connection elements along a first connecting direction, each second connection element having a second electrical contact element that is positioned and arranged such that electrical connection with a respective one of the first electrical contact elements is possible in both of two ways, one when the pneumatic connection of the respective ventilation tube to the liquid container is effected after the liquid container (Continued)

has been inserted into the housing and the other when the liquid container is inserted into the housing after the pneumatic connection of the ventilation tubes to the liquid container has been effected.

10 Claims, 6 Drawing Sheets

(51) Int. Cl.
    *A61M 16/10*     (2006.01)
    *A61M 16/00*     (2006.01)
    *H01R 13/00*     (2006.01)

(52) U.S. Cl.
    CPC .... *A61M 16/0816* (2013.01); *A61M 16/0875* (2013.01); *A61M 16/1095* (2014.02); *A61M 16/16* (2013.01); *H01R 13/005* (2013.01); *A61M 16/022* (2017.08); *A61M 16/1075* (2013.01); *A61M 2016/0036* (2013.01); *A61M 2205/14* (2013.01); *A61M 2205/3368* (2013.01); *A61M 2205/3653* (2013.01)

(58) Field of Classification Search
    CPC ...... A61M 2205/14; A61M 2205/3368; A61M 2205/3653; A61M 16/0833; A61M 16/1095; A61M 16/0003; A61M 16/0057; A61M 2016/0036; H01R 13/005; Y10S 261/31
    USPC ............ 128/202.27, 203.12, 203.26, 203.27, 128/204.14, 204.17; 138/118; 261/DIG. 31; 439/191
    See application file for complete search history.

(56) References Cited

U.S. PATENT DOCUMENTS

2011/0023874 A1*   2/2011   Bath ................ A61M 16/0066
                                                                                      128/202.22
2011/0159712 A1     6/2011   Chang

* cited by examiner

CONNECTING-SYSTEM KIT FOR A RESPIRATORY HUMIDIFIER

RELATED APPLICATIONS

This is a continuation of Ser. No. 14/348,969, filed Apr. 1, 2014, which was based on PCT/EP2012/069125, filed Sep. 27, 2012, which claims priority to German Patent Application No. DE 10 2011 054 134.9, filed Oct. 1, 2011, the contents of which are incorporated by reference in their entireties.

FIELD OF INVENTION

The present invention relates to respiratory humidifiers for ventilation of patients with breathing gas, and more specifically to connecting systems for respiratory humidifiers.

BACKGROUND OF THE INVENTION

When patients are being mechanically ventilated on an intensive-care ward, for example, the patient to be ventilated is connected pneumatically to the ventilator or respirator by a system of ventilation tubing. Because the breathing gas supplied to the patient must be adjusted with respect to temperature and humidity to meet the physiological needs of the patient, a respiratory humidifier is arranged in the inhalation or inspiration tube to heat and humidify the breathing gas. The respiratory humidifier comprises a liquid container filled with distilled water, through which the breathing air is conducted and humidified.

To prevent moisture from condensing inside the system of ventilation tubing, the inhalation tube and expiration or exhalation tube are usually provided with electrical tube heaters to heat the flowing inhalation or exhalation gas during operation. Loops of heating wire, for example, are used, which are integrated into the inhalation and exhalation tubes, or the inhalation and exhalation tubes are wrapped with coils of heating wire.

The breathing air temperature is usually regulated by means of a temperature sensor arranged near the patient; the sensor is connected by means of an electrical measurement line to a control unit, which is installed in the respiratory humidifier, for example. It is therefore logical to design the electrical contact elements of the electrical lines on the tube connectors jointly with the pneumatic connection elements in order to minimize the number of separate connections.

Pneumatic tube couplers with electrical contact elements integrated into them are described in, for example, EP 1 127 583 A2; DE 199 58 296 C1; DE 197 25 875 A1; and US 2003/0059213 A1. A system which connects the two functional components of the inhalation tube to the respiratory humidifier is known from EP 1 369 141 A1. The connection element or tube coupler comprises a male plug section on the liquid container of the respiratory humidifier, onto which a female sleeve section at the end of the inhalation tube can be placed. Electrical contact elements are arranged laterally on the sleeve section of the inhalation tube; when the sleeve section is placed on the plug section, these elements are brought into contact with another electrical contact on the housing of the respiratory humidifier to establish the electrical connection.

The disadvantage of the tube connecting system described in EP 1 369 141 A1 is that it can be placed onto the respiratory humidifier in only one direction, namely, from above. Before the connection is made, the electrical contact elements on the housing project awkwardly from the housing as independent elements and thus interfere with the appearance and practicality of the respiratory humidifier. Another disadvantage arising from this connecting system is that it limits the scope of possibilities for designing the respiratory humidifier. Logical improvements in this regard are therefore almost impossible to make with the existing devices.

It is therefore the object of the present invention to provide a connecting system for connecting a ventilation tube to a respiratory humidifier, which system offers a variety of ways in which the electrical contact elements can be connected to each other and which thus makes it possible to improve the design and appearance of the respiratory humidifier. It is also an object of this invention to provide a convenient kit including the liquid container and the tubing having such advantages.

SUMMARY OF THE INVENTION

According to one aspect of the invention, a connecting system for connecting a ventilation tube to a respiratory humidifier is provided, wherein the ventilation tube comprises an electrical line and the respiratory humidifier comprises a housing and a liquid container, the connecting system including a first connection element arranged on the liquid container, a first electrical contact element arranged on the housing, a second connection element, which can be connected to the ventilation tube, and a second electrical contact element, which can be connected to the electrical line of the ventilation tube, wherein the first connection element and the second connection element can be connected to each other in a first connecting direction in such a way that, through the establishment of the pneumatic connection of the ventilation tube with the liquid container, the electrical connection of the first contact element with the second contact element is also achieved.

The connection system is characterized in that the electrical connection of the first contact element with the second contact element can be established in a second connecting direction different from the first connecting direction, preferably in a direction essentially perpendicular to the first connecting direction. This offers the advantage that the liquid container with the ventilation tube or with several ventilation tubes connected to it can be slid sideways, for example, into the housing of the respiratory humidifier, which thus facilitates a compact design for the respiratory humidifier.

It should be noted here that the tubing and connecting systems and the liquid containers for ventilators used in hospitals are frequently designed as single-use or disposable articles, and it is therefore logical to provide as many of the connections as possible on the single-use parts, so that the operating personnel are required to perform only a small number of connection procedures. As a result, the operating time is significantly reduced, and the risk of connecting the components improperly is minimized. In the situation present before the liquid container and the ventilation tube are connected together, the inventive connecting system offers the possibility of connecting the tube before or after the liquid container has been inserted into the housing of the respiratory humidifier. The lateral insertion of the liquid container/ventilation tube kit thus opens up the possibility of new and advantageous design alternatives.

The first and second connection elements are preferably tubular in design and comprise a circular cross section. The first and second connection elements are preferably able to slide axially into each other in the first connecting direction. It is obvious that the circular cross section pertains essentially to the pneumatic connection between the ventilation tube and the liquid container. At least certain parts of the electrical contact elements are then arranged around this cross section. Other cross-sectional shapes such as rectangular, elliptical, or polygonal, are also possible.

It is also advantageous for the second connection element to comprise an external projection, which engages for guidance in a recess in the first connection element or in the housing of the respiratory humidifier. The ventilation tube and the liquid container can thus be connected to each other in a previously determined manner, namely, in a manner determined by the guide elements. It is possible to arrange several guides on the corresponding elements. It has been found adequate, however, and especially effective to provide exactly one guide element per connecting system.

It is also preferable for each of the first and second electrical contact elements to comprise a plurality of electrical contacts. It is advisable here for the first and second contact elements to have the same number of electrical contacts. It has been found that six electrical contacts per electrical contact element offer sufficient opportunities for transmitting electrical heating power, data, and measurement values, for example, via the ventilation tube system.

It is especially advantageous for the establishment of the proper pneumatic and electrical connections between the first and second connection elements to result in the closure of an electrical signal pathway. Thus the fact that all of the connections have been properly established can be displayed on the display device, for example, of the respiratory humidifier. Alternatively, other types of optical and even acoustic signals are also possible.

The first electrical contact element preferably comprises recesses, into which mating projections of the second electrical contact element engage in order to establish the electrical connection. The recesses and projections will thus be located next to each other, will be accessible from two directions, i.e., from above and from the side, and can comprise different materials and dimensions, depending on the power to be transmitted or the stability of the electrical contact connection. In a similar manner, the electrical contact elements can be provided with one or more springs.

It is advantageous for the ventilation tube to comprise a plurality of electrical lines, wherein preferably (at least) one is designed as a heating wire loop or heating wire coil, a power supply line, a measurement line, or a data line. Thus it is also possible not only for data or signals to be evaluated in the respiratory humidifier but also, for example, for signals to be sent from the patient to the respiratory humidifier or vice versa.

Also according to an aspect of the invention is a ventilation system comprising a ventilator, a first inhalation tube, a second inhalation tube, a respiratory humidifier, and two connecting systems as described above, wherein the two connecting systems connect the first and second inhalation tubes to the respiratory humidifier.

It is especially advantageous that the first inhalation tube and the second inhalation tube can be connected by the use of either the first or the second connecting system, wherein the flow direction of the breathing gas can be recognized on the basis of the electrical contact elements. The respiratory humidifier can be thus be used flexibly, for it recognizes where the inhalation tube leading to the ventilator, i.e., to the source of the breathing air, is connected and then determines on this basis the direction in which the breathing air should flow through the respiratory humidifier. Operating errors by the user are thus further reduced, because reversing the connection of the inhalation tubes no longer leads to a malfunction.

BRIEF DESCRIPTION OF THE DRAWINGS

The invention is to be explained below on the basis of exemplary embodiments with reference to the attached figures.

DETAILED DESCRIPTION

Figure 1:
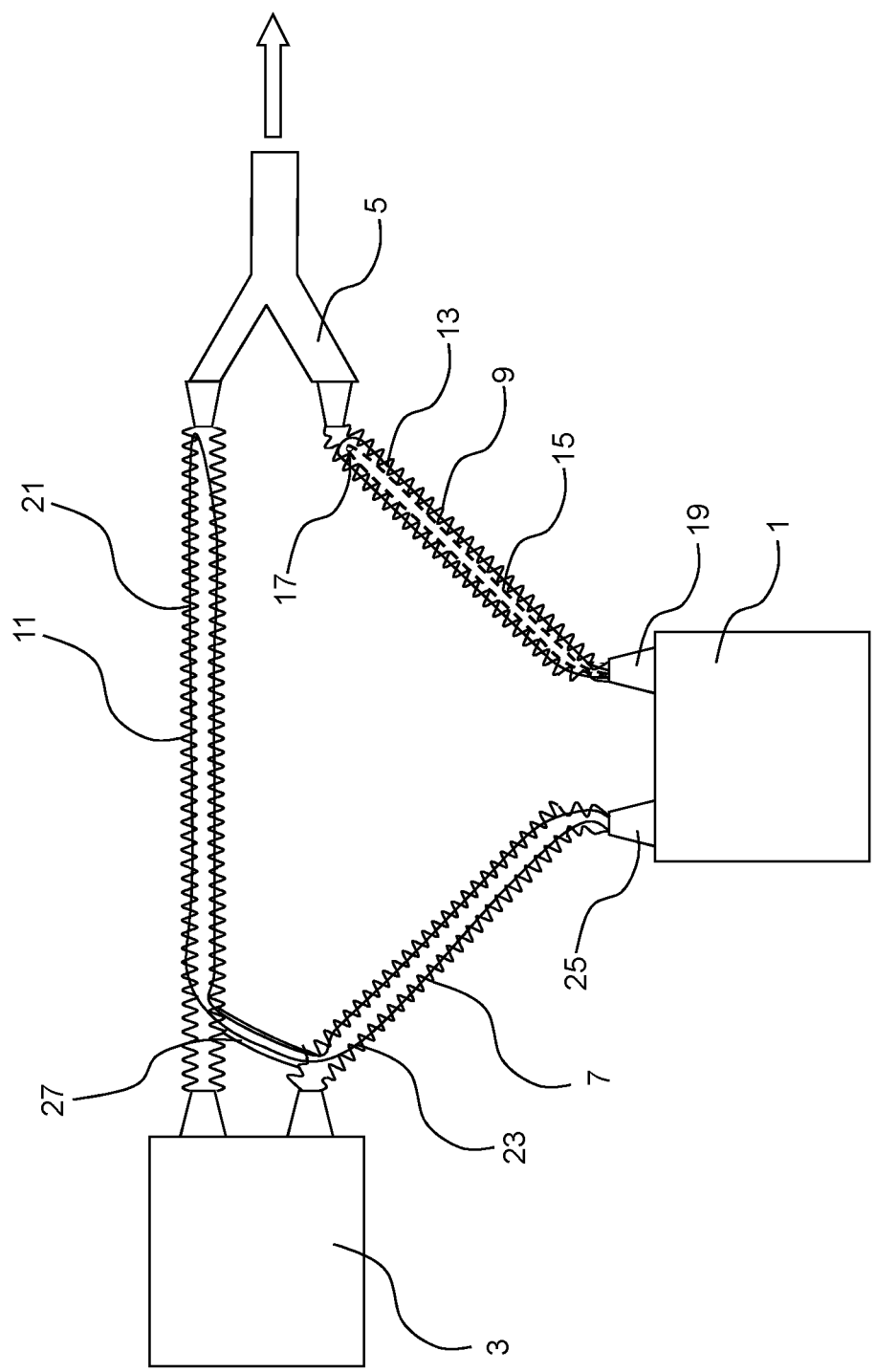
FIG. 1 is a schematic diagram of one embodiment of the ventilation system according to the present invention.

FIG. 1 schematically shows a preferred embodiment of a ventilation system having a connecting system according to the invention. A respiratory humidifier 1 is arranged between a respirator 3 and a Y-piece 5 and connected to them by a first inhalation or inspiration tube 7 and a second inhalation or inspiration tube 9. The simply designed end of the Y-piece 5 is pointing toward the patient to be ventilated, as indicated by the arrow. Finally, an exhalation or expiration tube 11 is arranged between the respirator 3 and the remaining end of the Y-piece 5.

A flow of dry breathing gas is produced by a blower (not shown), for example, in the respirator 3; this gas leaves the ventilator through the first inhalation tube 7 and proceeds toward the respiratory humidifier 1. There the breathing gas is conducted in the known manner into a liquid container (not shown in FIG. 1), where it is heated and humidified by the heated liquid. The heated and humidified breathing gas leaves the respiratory humidifier 1 via the second inhalation tube 9 and is supplied to the patient via the Y-piece 5.

In accordance with a breathing cycle controlled by the respirator 3, the spent breathing air flows back from the patient, enters the exhalation tube 11 at the Y-piece 5, and returns to the respirator 3.

A heating wire 13 is integrated into the wall of the second inhalation tube 9; this wire is wound into a spiral and serves as a heating coil. Also integrated into the second inhalation tube 9 is an electrical measuring line 15, which transmits the signal from a temperature sensor 17 arranged at the end near the Y-piece 5 to the control unit (not shown) of the breathing air humidifier 1. The location of the temperature sensor 17 is selected so that it is as close as possible to the patient but is still a part of the ventilation tube system, which is designed to be as easy as possible to replace.

The pneumatic and electrical connections of the second inhalation tube 9 to the respiratory humidifier 1, that is, the inhalation gas connection and the connections of the heating wire 13 and the measurement line 15, are achieved by means of a first connecting system 19.

The exhalation tube 11 also comprises a tube heater in the form of the heating wire 21, which is also wound into a spiral to form a heating coil. The reason for heating the exhalation tube 11 is to prevent the breathing gas returning from the patient from condensing in the exhalation tube 11 and flowing as contaminated liquid, for example, back to the patient through the Y-piece 5. The tube heater of the exhalation tube 11 can be continuous or be formed in sections. The heating wire 21 is supplied with current through a power supply line 23, which starts from the respiratory humidifier 1 and proceeds via a second connecting system 25, the first inhalation tube 7, and a connection element 27 to the exhalation tube 11. The second connecting system 25 thus represents the pneumatic and electrical connection of the first inhalation tube 7 to the respiratory humidifier 1, that is, the inhalation gas connection and the connection of the power supply line 23.

Figure 2:
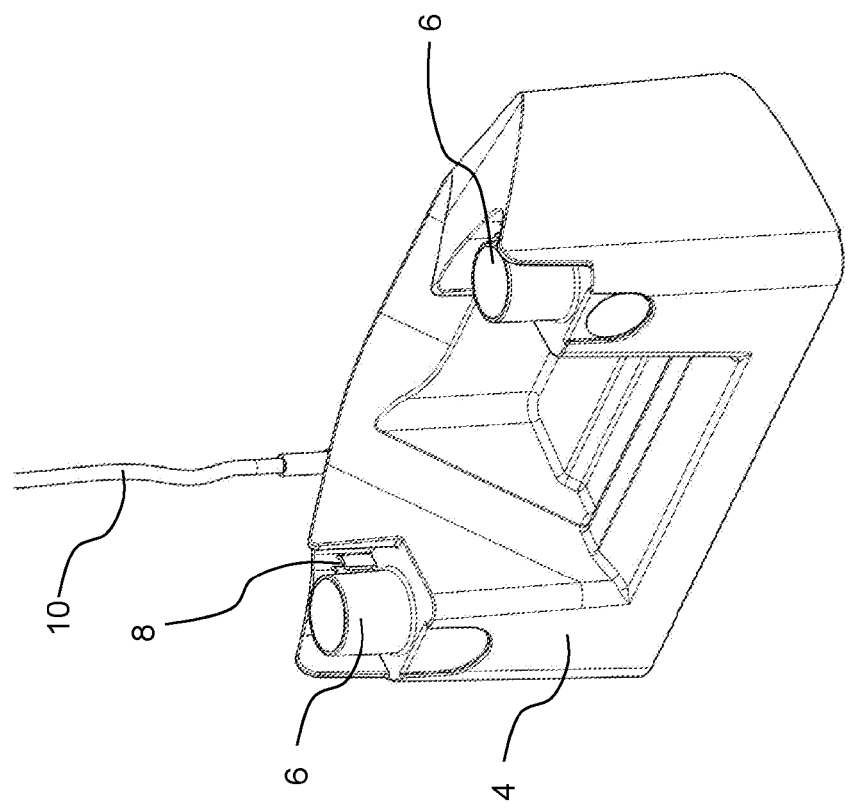
FIG. 2 is a perspective view of a liquid container with parts of a preferred embodiment of the connecting system according to the invention.

FIG. 2 shows a perspective view of a liquid container 4 with parts of a preferred embodiment of the connecting system according to the invention. The liquid container 4 comprises two first connection elements 6, which are arranged at the sides of the upper section. Between the two connection elements 6 a recess is formed, which is designed to mate with the housing projection (not shown in FIG. 2), so that the container can be pushed into the housing around the projection, as shown in FIGS. 4-7. The first connection elements 6 are designed as projecting tubular sockets with a circular cross section, but they may also have an elliptical or polygonal or even rectangular cross section.

A short distance away from each of the first connection elements 6, that is, at a distance sufficient to allow the second connection elements 14 to be pushed on, there is a guide 8, which serves to align the second connection element 14 axially so that it can be pushed easily onto the first connection element 6. It can also be seen that the first connection elements 6 do not project beyond the edge of the liquid container 4. This offers the advantage that they are less susceptible to damage if the liquid container 4 were to fall onto its back or top. A refill tube 10 is connected to the liquid container 4 by a suitable connecting piece. Because the internal volume of the liquid container 4 is limited, fresh water is supplied through the refill tube 10 when the water in the interior of the liquid container 4 falls below a certain level. The material of the liquid container 4 is a suitable transparent plastic such as polyethylene (PE) or polypropylene (PP). Other suitable plastic materials can also be used, however.

Figure 3:
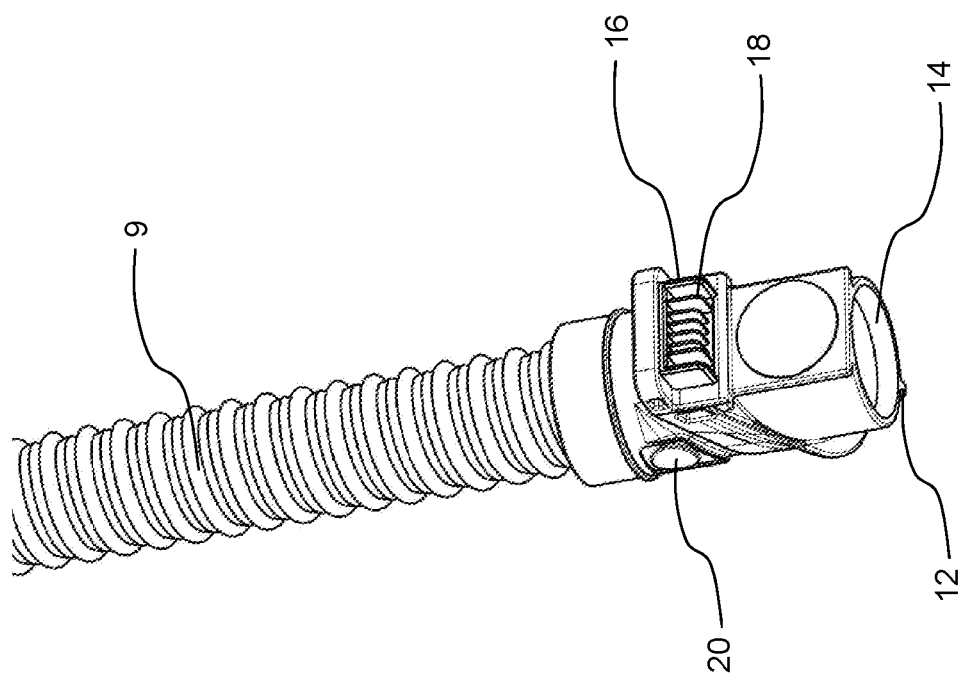
FIG. 3 is a perspective view of an inhalation tube with parts of the preferred embodiment of the connecting system according to the invention.

FIG. 3 shows a perspective view of an inhalation tube 9 with parts of the preferred embodiment of the connecting system according to the present invention. One end of the first inhalation tube 9 forms a connecting piece; the end of this connecting piece facing way from the tube is formed by the second connection element 14. The connecting piece also comprises a second electrical contact element 16, which is arranged on one side of the connecting piece. It is equipped with electrical contacts, which are designed as projections 18. The connecting piece also comprises gripping elements 20, which are also located on the sides, namely, about 901 away from the second electrical contact element 16, and which serve as points where force can be exerted to separate the connection. On the side opposite the second electrical contact element 16, the second connection element 14 comprises an elongated projection 12 on the outside surface, which extends in the axial direction and which is able to engage in the guide 8, which is shown in FIG. 2. To achieve a design which is attractive in both an optical and haptic sense, the connecting piece comprises a slanted skirt, which, when the connecting system is in the assembled state on the liquid container 4, is intended to create an essentially closed covering surface.

In the preferred embodiment, the second connection element 14 is pushed all the way onto the first connection element 6 along the guide; that is, it is pushed with a press fit all the way down until it rests on the liquid container 4, which acts as a stop. Alternatively, a latching mechanism can be arranged between the two connection elements 6, 14, which can be released again by pressing on the gripping elements 20, for example.

Figure 4:
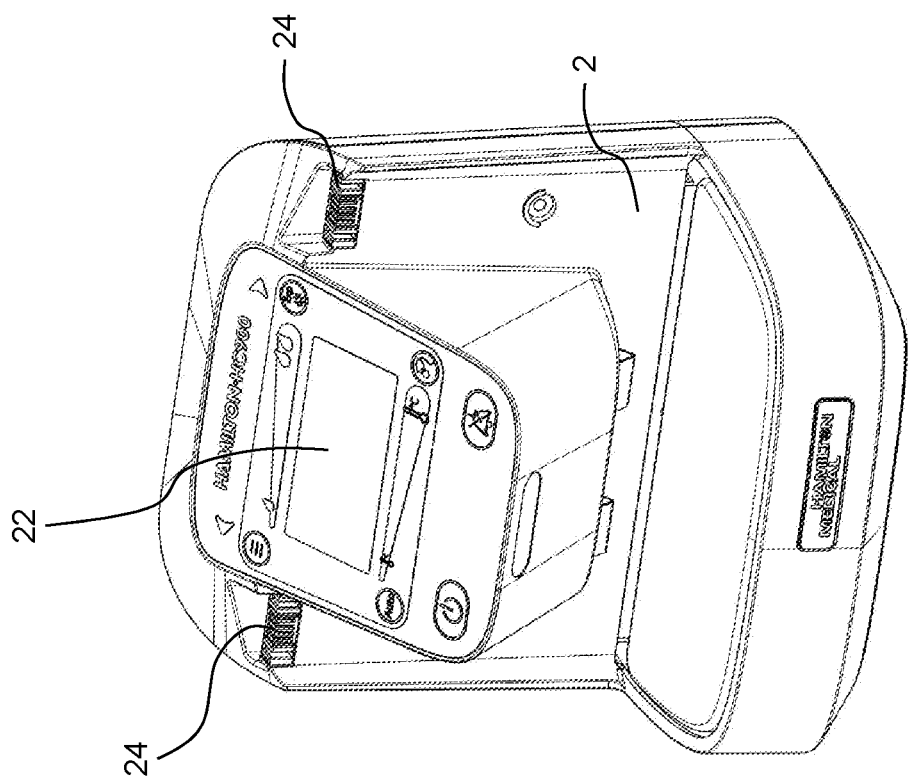
FIG. 4 is a perspective view of a housing of a respiratory humidifier with parts of the preferred embodiment of the connecting system according to the invention.

FIG. 4 shows a perspective view of a housing 2 of a respiratory humidifier 1 with parts of the preferred embodiment of the connecting system according to the present invention. The housing 2 has essentially the shape of an "L" with a horizontal part and a vertical part and comprises a heating plate on the horizontal part, which serves to heat the liquid in the liquid container 4 (not shown in FIG. 4). Extending from approximately the middle of the free end of the vertical part, the housing 2 comprises a slanting, projecting section, which comprises a user interface 22, provided with a display unit and operating elements. The interior of the housing 2 comprises, among other things, a control unit, which is able, for example, to regulate the output of the heating plate on the basis of the signals received from various temperature sensors. The housing 2 can also comprise other functional elements not belonging to the scope of the present invention. At the sides of the upper area of the vertical section of the housing 2, first electrical contact elements 24 are formed, which fit together with the second electrical contact elements 16 on the connecting piece shown in FIG. 3.

Figure 5:
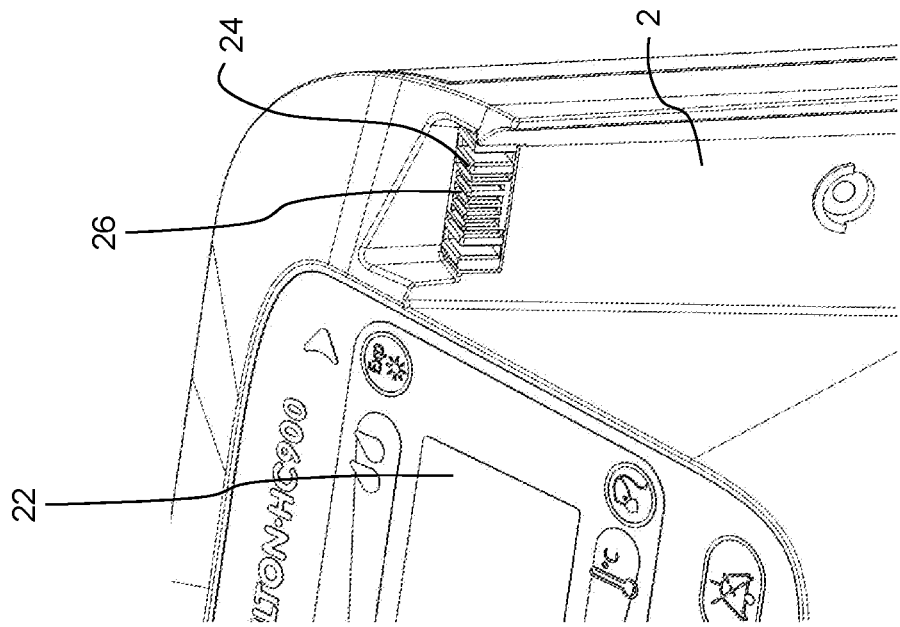
FIG. 5 is an enlarged detail of FIG. 4.

FIG. 5 shows an illustration on an enlarged scale of the upper right area of FIG. 4. It can be seen that the first electrical contact element 24 is arranged at the upper end of an essentially vertical housing wall and is set into a notch, wherein the electrical contacts are formed by recesses 26, which mate exactly with the projections 18 of the second electrical contact element 16 (see FIG. 3). It can be derived from a joint consideration of the electrical contact elements 16 and 24 as shown in FIGS. 3 and 5 that the electrical connection between the connecting piece of FIG. 3 and the housing 2 of FIG. 4 can occur both by insertion from the top and also by lateral insertion in the horizontal direction.

Figure 6:
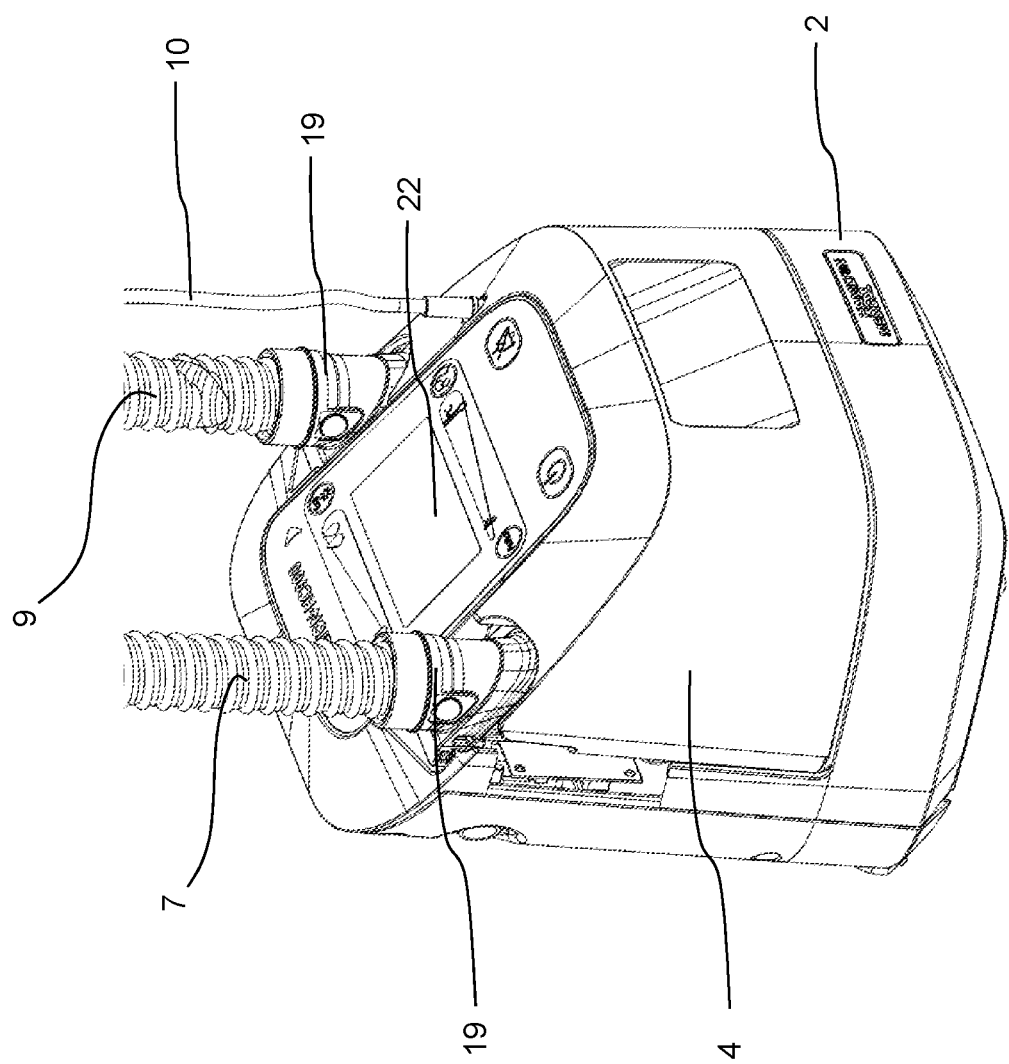
FIG. 6 is a perspective view of a respiratory humidifier with two connecting systems according to the preferred embodiment.

FIG. 6 shows a perspective view of a respiratory humidifier with two inventive connecting systems according to the preferred embodiment of the present invention. The object of FIG. 6 can be seen in the combination of the liquid container 4 of FIG. 2 with the tube connecting piece of FIG. 3 (two of which are present) and the housing 2 shown in FIG. 4. The liquid container 4 here has been pushed horizontally into the open area of the housing 2, so that the bottom section of the liquid container 4 lies essentially on the lower section of the housing 2, where the heating plate of the respiratory humidifier 1 is located. A connecting piece, one of which is located at the end of each of the two inhalation tubes 7, 9, is pushed onto each of the two first connection elements 6.

In the situation present before the liquid container 4 has been installed in the housing 2, the only effect of setting the second connection element 14 onto the opposing part, namely, the first connection element 6, so that the projection 12 fits within the guide 8, is that of establishing the pneumatic connection between the tube and the liquid container 4. The electrical connection between the electrical measurement, heating, or data lines in the tubes 7, 9 and the housing 2 can be established in either of two different ways.

Figure 7:
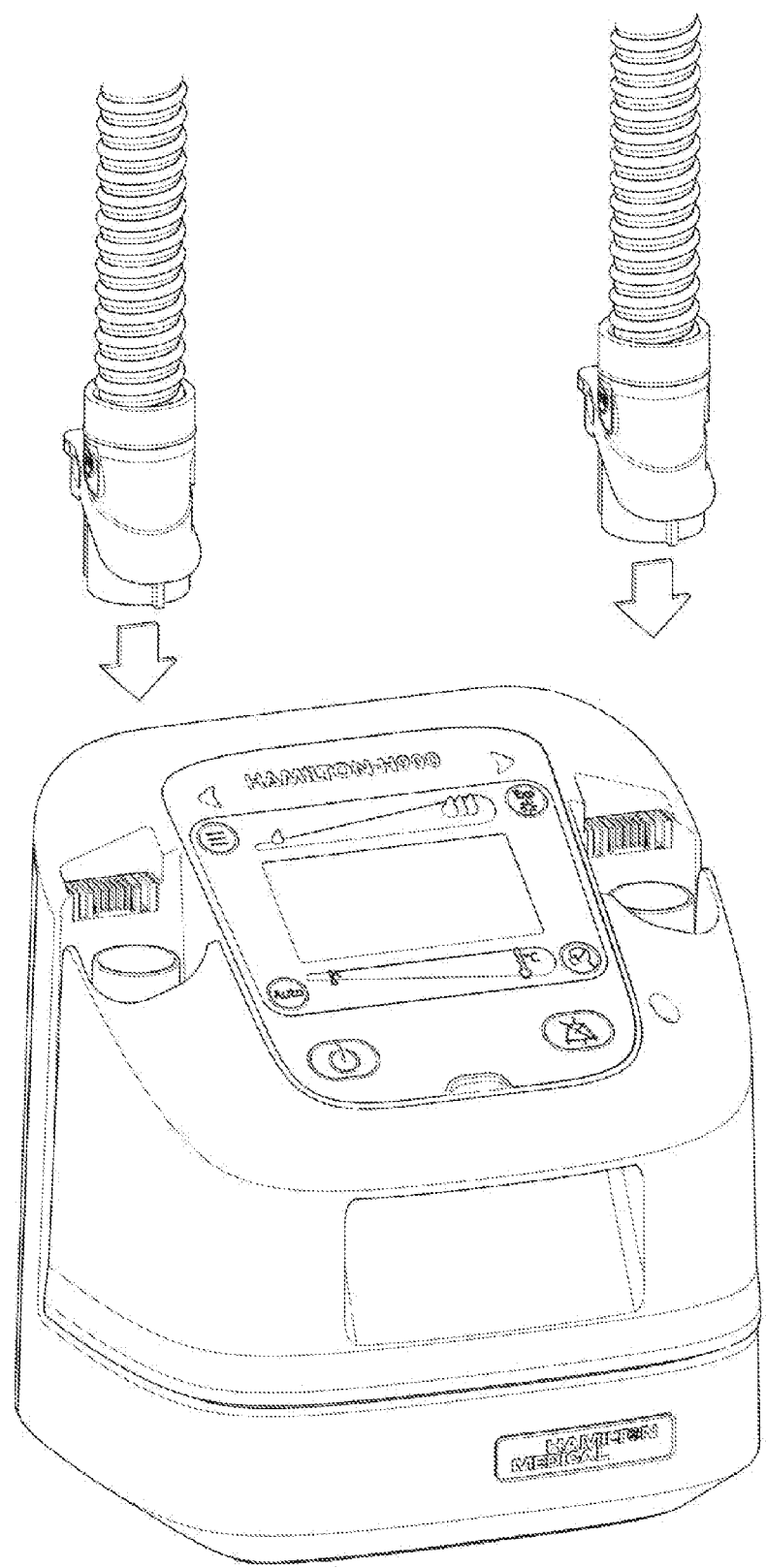
FIG. 7 is a perspective view of a respiratory humidifier illustrating the first connecting direction according to the invention.

The first possibility is to insert the liquid container 4 into the housing 2 and then to put the tubes 7, 9 in place by means of the connecting system, as a result of which the pneumatic and electrical connections are established simultaneously as seen in FIG. 7. The connecting direction in this case is vertically from above, in the axial direction of the ends of the tubes.

Figure 8:
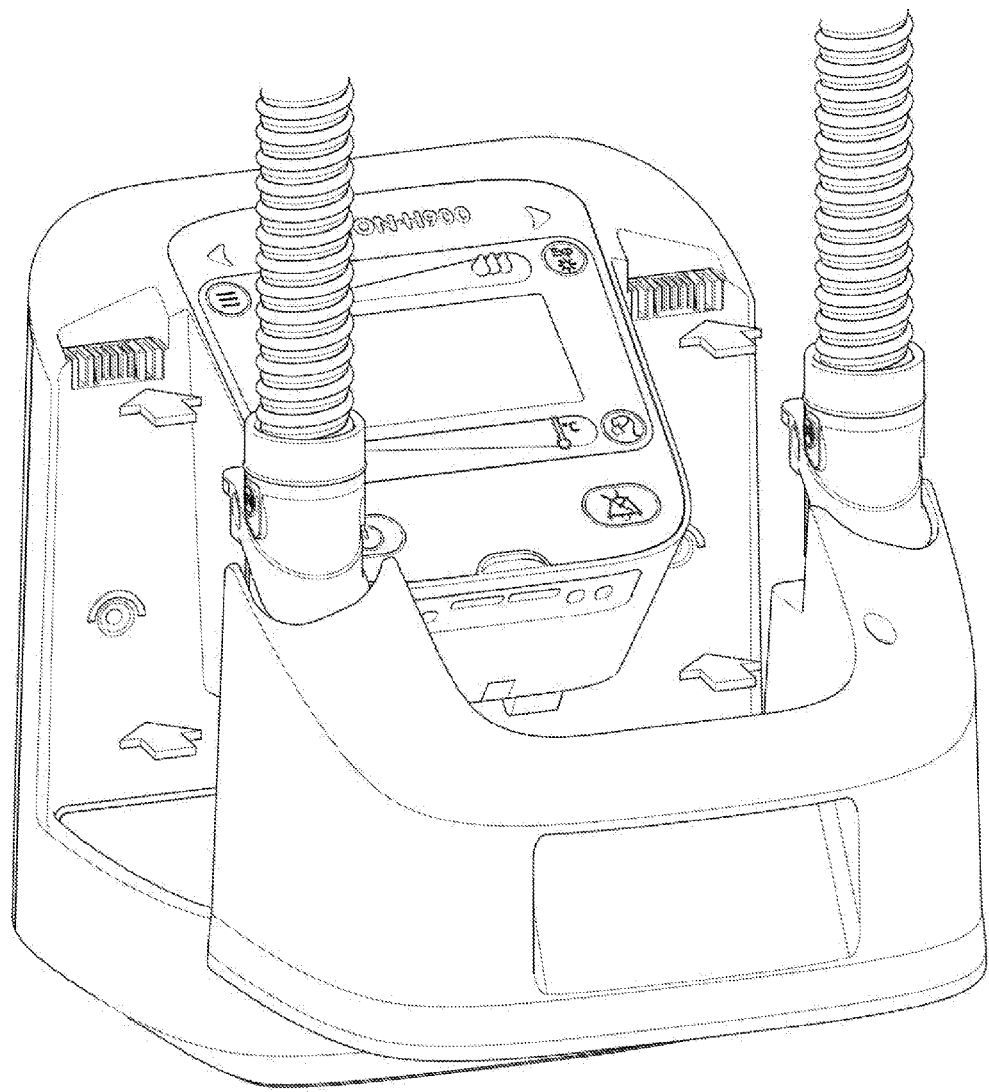
FIG. 8 is a perspective view of a respiratory humidifier illustrating the second connecting direction according to the invention.

The second possibility, illustrated in FIG. 8, will be used more frequently in cases where the ventilation tube systems are designed as single-use/disposable articles, because the liquid container 4 will usually be delivered together with a complete ventilation tube system, that is, together with the first inhalation tube 7, the second inhalation tube 9, and the exhalation tube 11 and possibly the Y-piece 5 (see FIG. 1), all connected together as a unit, so that the operating personnel are required to perform the minimum number of connecting steps. To connect the liquid container 4 to the housing 2 of the respiratory humidifier, the liquid container is inserted into the housing 2 horizontally, that is, in a direction perpendicular to the direction of the tubing and to the direction in which the pneumatic lines are connected. The liquid container 4 and the housing 2 are designed in such a way that the liquid container 4 latches in place in a manner which is perceptible to the user. FIG. 6 shows the latched end position of the liquid container 4 in the housing 2, and when the liquid container 4 latches itself in place in the housing 2, the electrical connection between the second electrical contact element 16 of the connecting pieces 7, 9 with the corresponding opposing pieces of the first electrical contact elements 24 is also established. Once all of the electrical and pneumatic connections have been properly established, the control unit can emit an acoustic signal or display the status on the user interface 22.

With the subject matter of the present invention, a connecting system for connecting a ventilation tube to a respiratory humidifier has been provided which offers flexible design possibilities for the electrical contact elements and thus enables an improved design as well as an attractive appearance of the respiratory humidifier. It should also be pointed out here that the connecting system according to the invention can also be used in principle to connect the second end of the first inhalation tube to the ventilator or also to connect the exhalation tube 11 to the respirator 3.

The invention claimed is:

1. A liquid-container/ventilation-tube kit for a ventilation system that includes (a) a ventilator, (b) a respiratory humidifier having a housing and a liquid container, the housing having a pair of first electrical contact elements, (c) a first inhalation tube extending from the respiratory humidifier to a Y-piece, (d) a second inhalation tube extending from the ventilator to the respiratory humidifier, and (e) an exhalation tube extending from the Y-piece to the ventilator, the liquid-container/ventilation-tube kit comprising:

the liquid container having a pair of first connection elements for removable connection of the first and second inhalation tubes thereto; and a pair of second connection elements each attached to a respective one of the first and second inhalation tubes and by which each of the inhalation tubes is pneumatically connected to a respective one of the first connection elements along a first connecting direction, each second connection element having a second electrical contact element connected to an electrical line extending along the respective inhalation tube, each second electrical contact element being positioned and arranged such that electrical connection with a respective one of the first electrical contact elements is possible in both of two ways, including: (i) in the first connecting direction when the pneumatic connection of the respective ventilation tube to the liquid container is effected after the liquid container has been inserted into the housing and (ii) by movement of the liquid container in a direction perpendicular to the first connecting direction when the liquid container is inserted into the housing after the pneumatic connection of the ventilation tubes to the liquid container has been effected.

2. The kit of claim 1 wherein the first and second connection elements are tubular with circular cross-sections and are slideably interengageable by relative axial motion thereof in the first connecting direction.

3. The kit of claim 2 wherein the second connection element comprises an external projection configured and arranged for engagement in a recess in the first connection element or in the housing of the respiratory humidifier to guide the connection of the second and first connection elements.

4. The kit of claim 1 wherein the first and second electrical contact elements each comprise a plurality of electrical contacts.

5. The kit of claim 4 wherein the first and second electrical contact elements each include six electrical contacts.

6. The kit of claim 1 wherein an electrical signal path is closed when the pneumatic and electrical connections between the first and second connection elements have been established.

7. The kit of claim 1 wherein the first electrical contact element comprises recesses into which mating projections of the second electrical contact element are engageable to establish electrical connection.

8. The kit of claim 1 wherein the ventilation tube includes a plurality of electrical lines.

9. The kit of claim 8 wherein the electrical lines include a heating wire loop or coil, a power supply line, a measurement line, or a data line.

10. The kit of claim 1 wherein the electrical line is a heating wire loop or coil, a power supply line, a measurement line, or a data line.

* * * * *